(12) United States Patent
Talton

(10) Patent No.: US 9,040,091 B2
(45) Date of Patent: May 26, 2015

(54) COMPOSITIONS AND METHODS FOR ORAL DELIVERY OF ENCAPSULATED DIETHYLENETRIAMINEPENTAACETATE PARTICLES

(71) Applicant: Nanotherapeutics, Inc., Alachua, FL (US)

(72) Inventor: James David Talton, Gainesville, FL (US)

(73) Assignee: NANOTHERAPEUTICS, INC., Alachua, FL (US)

( * ) Notice: Subject to any disclaimer, the term of this patent is extended or adjusted under 35 U.S.C. 154(b) by 84 days.

(21) Appl. No.: 13/827,667

(22) Filed: Mar. 14, 2013

(65) Prior Publication Data

US 2013/0251815 A1 Sep. 26, 2013

Related U.S. Application Data

(60) Provisional application No. 61/771,873, filed on Mar. 3, 2013, provisional application No. 61/614,333, filed on Mar. 22, 2012.

(51) Int. Cl.

| | | |
|---|---|---|
| *A61K 9/50* | (2006.01) | |
| *A61K 31/198* | (2006.01) | |
| *A61K 9/16* | (2006.01) | |
| *A61K 9/48* | (2006.01) | |
| *A61K 31/315* | (2006.01) | |
| *A61K 9/14* | (2006.01) | |
| *A61K 33/30* | (2006.01) | |

(52) U.S. Cl.
CPC ............ *A61K 31/198* (2013.01); *A61K 9/1647* (2013.01); *A61K 9/4891* (2013.01); *A61K 31/315* (2013.01); *A61K 9/14* (2013.01); *A61K 33/30* (2013.01)

(58) Field of Classification Search
CPC .................................................... A61K 9/1614
See application file for complete search history.

(56) References Cited

U.S. PATENT DOCUMENTS 7,910,086 B1 * 3/2011 Sung et al. .................. 424/1.69
2007/0196273 A1 8/2007 Shankar et al.

FOREIGN PATENT DOCUMENTS

WO WO 2007/008480 A1 1/2007

OTHER PUBLICATIONS

International Search Report and Written Opinion from International Application No. PCT/US2013/031336 mailed May 13, 2013.
Anonymous, "Nanotherapeutics Gets FDA Orphan-Drug Status for NanoDTPA TM Capsules to Treat Radiation Exposure", Jun. 22, 2011, XP002695836, retrieved from the Internet: URL:http://www.prweb.com/releases/2011/6/prweb8590302.htm.
Reddy, Joseph D, et al., "Preclinical Toxicology, Pharmacology, and Efficacy of a Novel Orally Administered Diethylenetriaminepentaacetic Acid (DTPA) Formulation", *Drug Development Research*, vol. 73, No. 5, Aug. 1, 2012, pp. 232-242, XP55060578, ISSN: 0272-4391, DOI: 10.1002/ddr.21018.

* cited by examiner

*Primary Examiner* — Carlos Azpuru
(74) *Attorney, Agent, or Firm* — Finnegan, Henderson, Farabow, Garrett & Dunner LLP

(57) ABSTRACT

The present disclosure is directed to compositions comprising encapsulated particles of diethylenetriaminepentaacetate (DTPA) and a zinc salt such as zinc acetate, and to pharmaceutical compositions comprising such encapsulated compositions. The present disclosure is also directed to methods of treatment by administering an effective amount of the compositions and pharmaceutical compositions of the present disclosure, to methods of making such encapsulated particle compositions, and to methods of making the corresponding pharmaceutical compositions.

13 Claims, No Drawings

COMPOSITIONS AND METHODS FOR ORAL DELIVERY OF ENCAPSULATED DIETHYLENETRIAMINEPENTAACETATE PARTICLES

This application claims the benefit of U.S. Provisional Application No. 61/614,333, filed Mar. 22, 2012, and U.S. Provisional Application No. 61/771,873, filed Mar. 3, 2013, both of which are both incorporated herein by reference.

This invention was made with Government support under HHSO100201100047C awarded by Biomedical Advanced Research and Development Authority (BARDA)/Office of Acquisitions Management, Contracts, and Grants (AMCG). The Government has certain rights in the invention.

The present disclosure relates generally to compositions comprising encapsulated particles of diethylenetriaminepentaacetate (DTPA) and a zinc salt such as zinc acetate, and to pharmaceutical compositions comprising such encapsulated compositions. It further relates to methods of making such encapsulated particle compositions, and to methods of making the corresponding pharmaceutical compositions. The encapsulated particle compositions described herein allow DTPA to be administered by routes that are non-invasive to patients, such as by oral administration.

Oral administration of drugs is generally preferred for reasons of patient comfort and compliance. However, many drugs, including DTPA, are highly polar at neutral pH, and are thus poorly or variably absorbed when delivered orally. Consequently, many such drugs are administered through more invasive routes, such as by inhaled or intravenous routes.

Several approaches for improving the oral delivery of poorly absorbed drugs are well-known in the art. For example, poorly soluble drugs may be administered as dispersions in large amounts of fatty acids, or milled to yield nanoparticles. There has been substantial effort in the last decade to produce drug particles from 100 nanometers to a few microns because of their improved dissolution properties (especially with insoluble drugs) and ability to be absorbed more efficiently. However, each of those approaches suffers from certain drawbacks, such as, e.g., inadequate stability, difficulty of manufacture, adverse interactions with the drug to be delivered, or the use of toxic amounts of permeation enhancers or enzyme inhibitors. Thus, there remains a need for compositions and methods for the non-invasive delivery of DTPA.

Dispersible nanoparticulate compositions, as described in U.S. Pat. No. 5,145,684 ("the 684 patent"), are particles less than approximately 400 nanometers in size consisting of a poorly soluble therapeutic or diagnostic agent having absorbed onto or associated with the surface thereof a non-crosslinked surface stabilizer. The '684 patent does not describe nanoparticulate compositions of DTPA. Methods of making nanoparticulate compositions are also described, for example, in U.S. Pat. Nos. 5,518,187 and 5,862,999, both for "Method of Grinding Pharmaceutical Substances", and U.S. Pat. No. 5,510,118 for "Process of preparing therapeutic compositions containing nanoparticles". Nanoparticles are prepared by dispersing a drug substance and surface modifiers in water and wet grinding in the presence of rigid grinding media, such as silica beads or a polymeric resin. These methods require removal of the grinding media and drying as additional steps to generate a dry nanoparticle product.

Cryogenic jet-milling with nitrogen is a well-suited size reduction technique for pharmaceutical powders that may be chemically degraded by mixing in aqueous media. Using cryogenic conditions while milling easily oxidized or heat-sensitive materials controls chemical decomposition, which can protect and enhance final product properties, produce finer particles/improve nanoparticle size yield, and increase the production rate (does not require additional steps for wet media milling described above). One method for cryogenic jet-milling with nitrogen is described in U.S. Pat. No. 8,074,906 "Process for milling and preparing powders and compositions produced thereby".

A composition comprising a DTPA chelate, including Zn-DTPA and Ca-DTPA, and a permeation enhancer that preferentially increases jejunal uptake of the DTPA chelate, is described in U.S. Pat. No. 7,914,767 ("the 767 patent"). The 767 patent composition describes a DTPA chelate bioavailability of at least 10% when orally administered. The incorporation of Zn-DTPA chelate, not a composition readily available, and a permeation enhancer that preferentially increases jejunal uptake of the DTPA chelate, which may have long-term toxicity in the gastrointestinal tract, is described in the 767 patent. The intestinal permeation enhancers include medium-chain glycerides, macrogolglycerides, polyglycols, and specifically caprylocaproyl macrogol-8-glyceride, as well as a P glycoprotein (Pgp) inhibitor in the 767 patent. The 767 patent composition is in the form of extruded beads contained within a capsule of an average diameter between 0.1-1 mm. There exists a need to be able to prepare particles of easily-available DTPA, not chelated, as well as without permeation enhancers that may produce unwanted long-term toxicity, to provide DTPA systemic uptake while minimizing the possibility of adverse physiological effects.

Accordingly, one aspect of the present disclosure provides an oral composition comprising particles of diethylenetriaminepentaacetate (DTPA) as a dry powder encapsulated by an enteric-coated polymer. In some embodiments, the particles of DTPA may have an average diameter ranging from about 0.1 micrometers to about 0.1 mm. The enteric-coated polymer may be, e.g., a polymer, including, e.g., a methacrylic acid copolymers (Eudragit L100). For example, in some embodiments, the present disclosure provides a composition comprising particles of DTPA encapsulated by Eudragit L100, wherein the DTPA content ranges from about 50% to about 80%. In some embodiments, the composition may further comprises a second compound to enhance DTPA solubility, such as, e.g., zinc acetate.

In certain embodiments, the present disclosure provides pharmaceutical compositions comprising particles of DTPA as a dry powder encapsulated by an enteric-coated polymer and may further comprise a second compound to enhance solubility of DTPA. In some embodiments, the solubility of DTPA may be enhanced by an amount greater than about 20% in aqueous solution by the addition of a second compound. Suitable second compounds include, e.g., a zinc salt. For example, in some embodiments, the present disclosure provides a pharmaceutical composition comprising a composition with improved aqueous solubility comprising particles of DTPA and zinc acetate.

In another aspect, the present disclosure provides a method of making a composition comprising particles of DTPA, the method comprising:
  blending DTPA together with a zinc salt to form a mixture;
  processing said mixture to form coarse particles having an average diameter ranging from about 0.1 mm to about 5 mm; and
  milling said coarse particles to form particles having an average diameter ranging from about 0.1 micrometers to about 0.1 mm.

In one embodiment, the milling step may comprise a jet-mill.

In yet another aspect, the disclosure provides a method of treating iron overload or radionuclide exposure, comprising administering an effective amount of a pharmaceutical composition of the present disclosure to a patient in need thereof.

I. Particulate Delivery Systems

In some embodiments, the present disclosure provides a composition (also referred to as a "particulate delivery system" or "PDS") comprising particles of a poorly absorbed drug, such as DTPA, encapsulated by a enteric-coated polymer. In some embodiments, the particles may have a diameter of, for example, less than 3 mm, less than 2 mm, less than 600 microns, less than 500 microns, or less than 300 microns. In some embodiments, the particles may have an average diameter less than about 0.1 mm (100 microns). For example, the particles may have a diameter of less than about 2.06 mm (corresponding to a 10 mesh sieve), less than about 1.68 mm (corresponding to a 12 mesh sieve), less than about 1.40 mm (corresponding to a 14 mesh sieve), less than about 1.20 mm (corresponding to a 16 mesh sieve), less than about 1.00 mm (corresponding to an 18 mesh sieve), less than about 0.853 mm (corresponding to a 20 mesh sieve), less than about 0.710 mm (corresponding to a 25 mesh sieve), less than about 0.599 mm (corresponding to a 30 mesh sieve), or less than about 0.500 mm (corresponding to a 35 mesh sieve). In some embodiments, the particles may have a diameter of less than about 300 microns, and may be able to pass through a 50 mesh sieve.

As used herein, the term "drug" encompasses the corresponding salts, hydrates, solvates, prodrugs, and complexes of a drug. Thus, a drug may be present as, e.g., a free base, a salt, a hydrate, a prodrug, a solvate (including a mixed solvate), or a complex (such as a pharmaceutically acceptable complex, and/or a complex with a polymer).

As used herein, the terms "poorly absorbed drug," "drug having low solubility," and the like refer to a drug (in its neutral (i.e., uncharged) state) having a water solubility in neutral pH buffer of less than about 20 mg/ml. For example, DTPA has a solubility in neutral pH buffer of <17.2 mg/ml. Thus, as used herein, DTPA (including DTPA and its salts, hydrates, solvates, complexes, etc.) is a poorly absorbed drug. The addition of a compound to enhance solubility, e.g., a zinc salt, at concentrations of about 10 mg/ml zinc acetate increases the solubility of DTPA by about 35% (about 23.3 mg/ml) and concentrations of about 20 mg/ml zinc acetate increases the solubility of DTPA by about 83% (about 31.5 mg/ml). In some embodiments, the present disclosure provides a pharmaceutical composition comprising a composition with improved aqueous solubility comprising a DTPA and zinc acetate composition of the present disclosure.

In some embodiments, a PDS according to the present disclosure may further comprise at least one additional compound, such as an additional drug. The additional drug may be chosen from, e.g., metal salts, anti-inflammatory drugs, and analgesics.

In some embodiments, a poorly absorbed drug may be present in the compositions and PDS of the present disclosure in an amount ranging from about <10% to about 90% of the PDS by mass. For example, a poorly absorbed drug may be present in an amount ranging from about 10% to about 90%, about 50% to about 90%, or about 50% to about 70% of the PDS, by mass. In some embodiments, the poorly absorbed drug may be present in an amount of about 65% by mass of the PDS. Further, in certain embodiments, the pharmaceutical composition comprising a composition with improved aqueous solubility may comprise DTPA in an amount of about 65% by mass of the composition, and zinc acetate present in an amount of about 35% by mass of the composition.

In some embodiments, an enteric-coated polymer may be Eudragit L100. In some embodiments, the enteric-coated polymer may be biodegradable. In some embodiments, the enteric-coated polymer may be bioerodable. In certain embodiments, the enteric-coated polymer may be considered by the FDA to be generally regarded as safe (GRAS).

II. Methods of Making a PDS

The present disclosure also provides a method of making a composition of the present disclosure comprising particles of a poorly absorbed drug encapsulated by an enteric-coated polymer, the method comprising:

blending DTPA together with a zinc salt to form a dry mixture;

processing said mixture to form coarse particles having an average diameter ranging from about 0.1 mm to about 5 mm; and jet-milling said coarse particles to form particles having an average diameter ranging from about 0.1 micrometers to about 0.1 mm.

In certain embodiments, the particles have an average diameter ranging from about 0.1 microns to about 0.1 mm. Particulate materials, also designated as "particles", to be produced in accordance with this disclosure are those in which small nanometer to micrometer size particles may be desirable. Examples may include nanoparticles and microparticle forms of pharmaceuticals, including poorly absorbed drugs. The possibilities and combinations are numerous.

In one embodiment, a system for preparing a composition of the present disclosure may include a venturi-type nozzle or 'Tee' valve to introduce cryogenic gas to, for example, a jet mill. Without wishing to be bound by any particular theory, combinations of dry gases at cryogenic temperatures (generally below 0° C.) before introduction into the jet mill may be used to eliminate moisture-induced agglomeration, as well as promote brittle fracture of particles upon impaction, and has been observed to act synergistically to produce a marked improvement in the particle size reduction efficiency. Cryogenic liquids suitable for use in this method include liquid argon, liquid nitrogen, liquid helium or any other liquefied gas having a temperature sufficiently low to produce brittle fracture of particles. The cryogenic liquid may also prevent milling losses and thermal damage to the feed material that would otherwise be caused by the volatization or overheating of constituent ingredients.

In one embodiment, a powder is placed in a temperature controlled vessel, such as a jacketed hopper or a screw-feeder, or is frozen beforehand. The cryogenic liquid and gas inputs are opened and the flow and temperature is set to the desired process conditions. The cryogenic gas input system, for example liquid nitrogen mixed with nitrogen gas, may be connected to a standard commercial jet mill, such as a Trost Gem-T, Trost T-15, Fluid Air Aljet, Hosikawa Alpine AS Spiral Jet Mill, Sturtevant Micronizer, or similar system, as the main carrier gas in a variety of gas input setups. Pre-run setup of the system may include attaching a temperature probe or flowmeter, such as a TSI Model 4040 Flowmeter or similar system, at the gas input or to the top of the cyclone (in place of air relief bag), setting the carrier gas on different input pressures and documenting the gas flow and temperature measurements (CFM). The milling process may be started by turning on the powder feeder and after passing powder through the milling region, the jet-milled powder is collected in the cup or similar receiver unit (typically particles ~1-10 microns) or from the bag above the cyclone (particles <1 micron), depending on the exact run conditions. Particles with diameters ranging from less than about 1 micron to about 10 micros may be produced by running the powder from the cup through the jet-mill under similar run conditions multiple times, or passes, to obtain the desired particle size.

In certain embodiments, the particles may have an average diameter ranging from about 0.1 mm (100 microns) to about 3 mm. For example, the particles may have a diameter of less than about 2.06 mm (corresponding to a 10 mesh sieve), less than about 1.68 mm (corresponding to a 12 mesh sieve), less than about 1.40 mm (corresponding to a 14 mesh sieve), less than about 1.20 mm (corresponding to a 16 mesh sieve), less than about 1.00 mm (corresponding to an 18 mesh sieve), less than about 0.853 mm (corresponding to a 20 mesh sieve), less than about 0.710 mm (corresponding to a 25 mesh sieve), less than about 0.599 mm (corresponding to a 30 mesh sieve), or less than about 0.500 mm (corresponding to a 35 mesh sieve). In some embodiments, the particles may have a diameter of less than about 300 microns, and may be able to pass through a 50 mesh sieve. In certain embodiments, the particles have a diameter of about 0.6 mm or less.

In certain embodiments, the enteric-coated polymer is heated prior to blending with the poorly absorbed drug.

In some embodiments, the present disclosure provides a method of making a composition of the present disclosure comprising particles of a poorly absorbed drug encapsulated by an enteric-coated polymer using a process wherein the process is at least partially a continuous manufacturing process. The method may comprises:

blending DTPA together with a zinc salt and an enteric-coated polymer to form a mixture;

heating said mixture to a temperature sufficient for extrusion of the mixture;

extruding said mixture to form coarse particles having an average diameter ranging from about 0.1 mm to about 5 mm;

cooling said coarse particles; and processing (e.g., by milling, grinding, or crushing) said coarse particles to form particles having an average diameter less than about 0.1 mm.

In certain embodiments, the particles may have an average diameter ranging from about 0.1 mm (100 microns) to about 3 mm. For example, the particles may have a diameter of less than about 2.06 mm (corresponding to a 10 mesh sieve), less than about 1.68 mm (corresponding to a 12 mesh sieve), less than about 1.40 mm (corresponding to a 14 mesh sieve), less than about 1.20 mm (corresponding to a 16 mesh sieve), less than about 1.00 mm (corresponding to an 18 mesh sieve), less than about 0.853 mm (corresponding to a 20 mesh sieve), less than about 0.710 mm (corresponding to a 25 mesh sieve), less than about 0.599 mm (corresponding to a 30 mesh sieve), or less than about 0.500 mm (corresponding to a 35 mesh sieve). In some embodiments, the particles may have a diameter of less than about 300 microns, and may be able to pass through a 50 mesh sieve. In certain embodiments, the particles may have a diameter of about 0.1 mm or less.

In certain embodiments, the enteric-coated polymer may be heated prior to blending with the poorly-absorbed drug.

III. Pharmaceutical Compositions (Final Dosage Forms)

The present disclosure further provides pharmaceutical compositions (sometimes referred to as "final dosage forms" or "FDF") comprising a compositions according to the present disclosure.

In some embodiments, the pharmaceutical compositions may further comprise at least one excipient (such as, e.g., a enteric-coated polymer, surfactant, and/or metal salt), such as a pharmaceutically acceptable excipient. Examples of pharmaceutically acceptable excipients may be, for example, those described in Remington's Pharmaceutical Sciences by E. W. Martin, and include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. In some embodiments, the pharmaceutical compositions also contain pH buffering reagents, and wetting or emulsifying agents.

In some embodiments, the pharmaceutical compositions may be formulated for oral administration. In this embodiment, the pharmaceutical composition may be in the form of, for example, tablets, capsules, or other oral dosage forms. Such oral dosage forms may be prepared by conventional means. The pharmaceutical composition can also be prepared as a liquid, for example as a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring, and sweetening agents. Alternatively, the composition can be presented as a dry product for constitution with water or another suitable vehicle.

For buccal and sublingual administration, the composition may take the form of tablets or lozenges according to conventional protocols.

The pharmaceutical composition can also be formulated for rectal administration as a suppository or retention enema, e.g., containing conventional suppository bases such as PEG, cocoa butter, or other glycerides.

In some embodiments, the pharmaceutical compositions described herein provide improved dissolution of the poorly absorbed drug, relative to the unencapsulated poorly soluble drug, and/or to another dosage form (such as, e.g., a more invasive dosage form). For example, dissolution may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by a Vankel tablet dissolution apparatus approved by the United States Pharmacopeia.

In some embodiments, the pharmaceutical compositions described herein provide improved oral bioavailability of the poorly soluble drug, relative to the unencapsulated poorly soluble drug, and/or to another dosage form (such as, e.g., a more invasive dosage form). For example, absorption may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by, e.g., in vivo pharmacokinetic studies in a preclinical animal model or human clinical evaluation.

In some embodiments, the pharmaceutical compositions described herein are immediate-release formulations. In such embodiments, the pharmaceutical compositions provide a more rapid onset of action of the poorly soluble drug, relative to the unencapsulated poorly soluble drug, and/or to another dosage form (such as, e.g., a more invasive dosage form). For example, the onset of action may be shortened by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by, e.g., in vivo pharmacokinetic studies in a preclinical animal model or human clinical evaluation.

In some embodiments, the pharmaceutical compositions described herein are controlled-release formulations. In such embodiments, the pharmaceutical compositions described herein provide a more rapid onset of action of the poorly absorbed drug.

In some embodiments, the pharmaceutical compositions described herein have reduced absorption variability, relative to the unencapsulated poorly absorbed drug, and/or to another dosage form (such as, e.g., a more invasive dosage form).

In some embodiments, the pharmaceutical compositions described herein are associated with improved patient compliance, relative to another pharmaceutical composition comprising the same poorly absorbed drug (which may be in another dosage form, such as, e.g., a more invasive dosage form).

IV. Methods of Making Pharmaceutical Compositions

In further embodiments, the present disclosure provides a method of making a pharmaceutical composition wherein the method further comprises formulating the particles.

In certain embodiments, the particles are formulated into unit doses such as tablets or capsules.

In some embodiments wherein the pharmaceutical compositions further comprises at least one excipient, the present disclosure also provides a method of making a pharmaceutical composition wherein the method further comprises mixing the particles with at least one excipient to form a second mixture; and formulating the second mixture.

In certain embodiments, the particles are formulated into unit doses such as tablets or capsules.

V. Methods of Treatment

The pharmaceutical compositions described herein may be useful to treat any disease or condition for which administration of a corresponding poorly absorbed drug is desirable. For example, compositions comprising DTPA may be useful for the treatment of iron overload or radionuclide exposure. The terms "treat," "treatment," and "treating" refer to (1) a reduction in severity or duration of a disease or condition, (2) the amelioration of one or more symptoms associated with a disease or condition without necessarily curing the disease or condition. In some embodiments, the method of treatment further comprises the prevention of a disease or condition. Suitable subjects include, e.g., humans and other mammals, such as, e.g., mice, rats, dogs, and non-human primates.

In certain embodiments, the present disclosure provides a method of treating iron overload or radionuclide exposure, comprising administering an effective amount of a pharmaceutical composition of the present disclosure to a subject in need thereof.

The following examples are merely illustrative, and should not be construed as limiting the present disclosure.

EXAMPLE 1

Preparation of NanoDTPA PDS

A mass of 64 g of DTPA (Merck, USP) and 36 g of zinc acetate (Spectrum, USP) was dry-mixed on a Turbula mixer. The powder was then ground into a fine powder using a Retsch mill. Particles smaller than 600 microns were separated by sieving (30 mesh). The mixture was transferred to a glovebox and placed in a Bransonic spoon feeder above a Fluid Air Aljet jet mill. A liquid and gas nitrogen mixture was adjusted resulting in a pressure of 120 psi (+/−10 psi) in each jet. The powder was fed into the mill over approximately 15 minutes and the resulting powder in the cup below the cyclone passed again through the mill five additional passes. The resulting white powder in the bag was obtained with a yield of >80 g NanoDTPA powder, containing particles with a diameter less than 100 microns and highly electrostatic.

EXAMPLE 2

Preparation of Oral Enteric-coated NanoDTPA Capsules

An sustained-release oral dosage form (gelatin capsules) containing the NanoDTPA particles prepared in Example 1 was prepared as described below. The NanoDTPA PDS prepared in Example 1 was dry mixed to achieve the correct capsule fill weight (400-500 mg) to achieve the desired dose. Clear gelatin #1 capsules were then filled with the mixture in a Fast-CAP Filling machine to yield capsules containing 470 mg of NanoDTPA (obtained from 300 mg diethylenetriaminepentaacetate and 170 mg zinc acetate). Enteric coating took place in a rotating-pan coater with sprayer attachment. The spray head was supplied with dry nitrogen gas feed and a peristaltic pump driven liquid feed. The coating was comprised of Eudragit L100 dissolved in a 97%/3% isopropanol/water solution. Samples were taken to verify loading uniformity, coating uniformity, content uniformity, and dissolution time.

EXAMPLE 3

Dissolution of Oral Enteric-coated NanoDTPA Capsules

An enteric-coated formulation was proposed to reduce the stomach exposure to DTPA, which is acidic in aqueous environment and may induce vomiting. Capsules were exposed to acidic buffer for 120 minutes to mimic the stomach environment. At the end of two hours, the pH was raised to neutral for 22 hours. To pass, there should be no more than 10% release of contents during the initial two hours in acidic buffer using a USP dissolution apparatus. Capsules were also submitted for content uniformity determined according to USP <905>.

EXAMPLE 4

Americium-241 Decorporation in Rats

The decorporation and excretion properties in rodents of oral NanoDTPA capsules at 60 mg/kg DTPA according to the present disclosure was compared to IV Zn-DTPA solution at 15 mg/kg DTPA, which is the currently licensed product available to the public. The studies were designed to provide data that systemic Am-241 at a single low dose followed by oral NanoDTPA capsules can provide a sufficient radiation dose reduction as an efficacy endpoint. All DTPA dosing was initiated 24 hours post-exposure to isotope (Am-241) in this set of studies to simulate a realistic emergency response time following exposure. Two sets of measurements were made: (1) internal tissue levels at 2, 4, and 7 days vs. (2) daily excreted concentrations in urine and feces.

There was not a significant difference in tissue content (lung, kidney, spleen, heart, and liver) or output (urine and feces) of Am-241 in animals treated with Zn-DTPA solution administered IV daily 15 mg/kg DTPA compared to NanoDTPA capsules administered PO 60 mg/kg DTPA observed when animals received 2-dose, 4-dose, or 7-dose treatments. Tissue concentrations following administration of either DTPA formulation were significantly lower compared to control animals receiving no DTPA treatment. Liver, the primary tissue that demonstrated Am-241 binding, demonstrated significantly reduced concentrations following IV Zn-DTPA and oral administration of NanoDTPA capsules according to the present disclosure compared to controls receiving no DTPA treatment after 2 (116.37+/−26.90 and 181.04+/−31.93 nCi vs. 594.85+/−158.75 nCi), 4 (81.70+/−11.53 and 137.94+/−28.40 nCi vs. 306.63+/−18.23 nCi), and 7 (55.42+/−19.68 and 114.32+/−61.10 nCi vs. 441.06+/−56.49 nCi) doses. There was a general trend of tissue reduction in all groups over the 3, 5, and 8 day observation period. All data are expressed as total Am-241 activity in nCi per 200 ul blood, homogenized tissue, or output (urine and feces). These preliminary studies demonstrate that oral NanoDTPA capsules according the present disclosure at 60 mg/kg DTPA are substantially equivalent to IV Zn-DTPA administered at 15 mg/kg, which is the highest dose available for the currently licensed product, in reduction of systemic Am-241 exposure.

EXAMPLE 5

Americium-241 Decorporation in Dogs

The objective of this study was to evaluate the concentration of DTPA in blood following a single administration with either Zn-DTPA injectable solution or NanoDTPA capsules using male beagle dogs. Single dose pharmacokinetic (PK) testing groups of Zn-DTPA solution vs. NanoDTPA capsules included nine study groups used for the PK testing. Zn-DTPA solution was delivered intravenously (IV) and by mouth (per os, PO) and NanoDTPA capsules were administered PO. The IV Zn-DTPA dose matched the current recommended dose for a 60 kg adult (1000 mg/60 kg=16.7 mg/kg Zn-DTPA, or 12.6 mg/kg DTPA). The Zn-DTPA doses delivered PO compared the current drug delivered at doses equivalent to $\frac{1}{10}\times$ and 1× of the proposed efficacious dose of NanoDTPA capsules. Three formulations of NanoDTPA capsules were tested to examine different formulations of NanoDTPA powder and different capsule sizes. The dose for each NanoDTPA capsule formulation was either two or six capsules and the calculated DTPA doses confirmed based on the amount of DTPA in the capsules and body weight.

The percent bioavailability of the Zn-DTPA solution delivered PO at a dose of 6 mg DTPA/kg was 12.26% at 72 hours post-dose. The percent bioavailability of the Zn-DTPA solution delivered PO at a dose of 60 mg DTPA/kg was 12.67% at 72 hours post-dose, respectively. The percent bioavailability of the size 1 NanoDTPA capsules at 55.9 and 172.6 mg DTPA/kg was 12.52% and 14.02% at 72 hours post-dose, respectively, demonstrating similar absorption of the Zn-DTPA solution delivered orally. The percent bioavailability following administration of uncoated size 1 NanoDTPA capsules at 58.8 mg DTPA/kg was 9.59% at 72 hours post-dose, demonstrating the improvement of enteric-coating the NanoDTPA capsule.

EXAMPLE 6

Americium-241 Decorporation in Dogs

The objective of this study was to evaluate the dose-related efficacy of daily doses of NanoDTPA capsules in male and female beagle dogs intravenously (IV) administered a soluble citrate complex of americium-241 (Am-241). Twenty-four (24) male and female beagle dogs underwent a 14-day quarantine period for acclimation. Once released from quarantine, animals were weighed and randomized into study animals or spares. The average body weight of study animals was 8.6±0.9 kg (males 9.0±1.0 kg; females 8.2±0.7 kg). After randomization, animals were acclimated to metabolism cages for 24 hours prior to radionuclide administration. Animals received a single IV administration of 241Am(III)-citrate on Day 0. One day after radionuclide administration, one of four different doses of NanoDTPA capsules [1, 2, or 6-capsules/day or 2 capsules twice/day], IV Zn-DTPA [15 mg/kg] as a positive control, or IV saline as a placebo were administered. NanoDTPA capsules, IV Zn-DTPA, or IV saline was administered on study days 1-14. Urine and feces were collected daily. Animals were euthanized on day 21 and tissues collected. Urine, fecal, and tissue samples were analyzed for Am-241 content.

The daily and cumulative urine sample data indicated statistically similar levels of urine excretion of Am-241 for all NanoDTPA capsule dose levels compared to the Zn-DTPA IV treatment. The Zn-DTPA treatment group exhibited approximately 9.4 times the Am-241 activity excreted in the urine compared to the saline placebo, and the NanoDTPA capsule dosages groups exhibited an increase of 7.6-9.5 times the Am-241 activity excreted in the urine compared to the saline placebo. The data from the liver and kidney samples indicate approximately 40 to 80% reduction in Am-241 remaining in the tissue following treatment with Zn-DTPA IV and oral NanoDTPA capsules compared to the saline placebo. All NanoDTPA Capsule dose groups appear statistically similar to the Zn-DTPA IV treatment.

EXAMPLE 7

28-Day Oral Capsule Toxicity Study in Dogs with NanoDTPA Capsules

The purpose of this study was to evaluate the toxicity of NanoDTPA capsules, when administered daily via oral capsule to dogs for at least 28 days and to assess the reversibility, persistence, or delayed occurrence of any effects after a 14 day recovery. Animals in the control group (Group 1) received six placebo capsules each day. Animals in the treated groups (Groups 2, 3, and 4) received 2, 6, or 12 capsules containing 300 mg active DTPA/capsule, or 60, 180, or 360 mg DTPA/kg/day. Assessment of toxicity was based on mortality, clinical signs, body weight, body weight change, food consumption, electrocardiography, ophthalmic observations, and clinical and anatomic pathology.

No test article-related deaths occurred over the course of the study. The incidence and frequency of nonformed and liquid feces generally increased with dose level and were considered test article-related. The increase in nonformed and liquid feces did not result in changes in the general condition of the animals or decreased weight gains and were not considered adverse. The incidence and frequency of vomiting were slightly increased in treated animals but the increases were not dose-responsive. The increase in vomiting may be related to the number of capsules administered/day since Group 2 animals received two capsules/day and had the lowest incidence of vomiting. No other test article related clinical observations were noted during the dosing or recovery phase. No test article-related alterations in mean body weights and overall body weight gain were noted during the dosing or recovery phases. No test article-related alterations in food consumption were noted during the dosing or recovery phases. The results demonstrate the safety of NanoDTPA capsules at all the doses tested.

Other embodiments of the present disclosure will be apparent to those skilled in the art from consideration of the specification and practice of the present disclosure disclosed herein. It is intended that the specification and examples be considered as exemplary only, with the true scope and spirit of the present disclosure.

What is claimed is:

1. A composition comprising particles of diethylenetriaminepentaacetate (DTPA) and a zinc salt, wherein the DTPA and the zinc salt are encapsulated by an enteric-coated polymer, and wherein the zinc salt is zinc acetate.

2. The composition of claim 1, wherein the particles have an average diameter of less than about 1 mm.

3. The composition of claim 2, wherein the particles have an average diameter of less than about 300 µm.

4. The composition of claim 3, wherein the particles have an average diameter of less than about 100 µm.

5. The composition of claim 1, wherein the DTPA is an acid.

6. The composition of claim 1, wherein the DTPA is a salt.

7. The composition of claim 1, wherein zinc acetate improves solubility of DTPA by an amount greater than about 20%.

8. The composition of claim 1, wherein the enteric-coated polymer is a water-soluble polymer.

9. The composition of claim 8, wherein the enteric-coated polymer is a methacrylic acid copolymer.

10. The composition of claim 1, wherein the DTPA is present in an amount ranging from about 0.01% to about 90% by mass of the composition.

11. The composition of claim 10, wherein the DTPA is present in an amount ranging from about 10% to about 90% by mass of the composition.

12. The composition of claim 11, wherein the DTPA is present in an amount ranging from about 50% to about 80% by mass of the composition.

13. The pharmaceutical composition of claim 1, wherein the composition is formulated for oral administration.

* * * * *